United States Patent
Fishman et al.

(10) Patent No.: US 7,465,715 B2
(45) Date of Patent: Dec. 16, 2008

(54) METHOD FOR TREATMENT OF MULTIPLE SCLEROSIS

(75) Inventors: Pnina Fishman, Herzliya (IL); Sara Bar Yehuda, Rishon le Zion (IL); Lea Madi, Rishon le Zion (IL)

(73) Assignee: Can-Fite Biopharma, Ltd., Petach Tikva (IL)

( * ) Notice: Subject to any disclaimer, the term of this patent is extended or adjusted under 35 U.S.C. 154(b) by 371 days.

(21) Appl. No.: 10/521,193

(22) PCT Filed: Dec. 23, 2004

(86) PCT No.: PCT/IL2004/001160

§ 371 (c)(1), (2), (4) Date: Jan. 13, 2005

(87) PCT Pub. No.: WO2005/063246

PCT Pub. Date: Jul. 14, 2005

(65) Prior Publication Data

US 2006/0142237 A1 Jun. 29, 2006

Related U.S. Application Data

(60) Provisional application No. 60/532,712, filed on Dec. 29, 2003.

(51) Int. Cl.
*A61K 31/70* (2006.01)
(52) U.S. Cl. ........................................................ 514/46
(58) Field of Classification Search ................ 514/46
See application file for complete search history.

(56) References Cited

U.S. PATENT DOCUMENTS

| 5,506,214 | A |   | 4/1996 | Beutler |
| 5,773,423 | A |   | 6/1998 | Jacobson et al. |
| 6,117,878 | A | * | 9/2000 | Linden .................. 514/263.34 |
| 6,303,619 | B1 | * | 10/2001 | Linden .................. 514/263.34 |
| 6,762,170 | B1 |   | 7/2004 | Chan et al. |
| 2002/0094974 | A1 |   | 7/2002 | Castelhano et al. |

FOREIGN PATENT DOCUMENTS

| WO | WO 95/11681 A1 |   | 5/1995 |
| WO | WO 97/33879 A1 |   | 9/1997 |
| WO | WO 2004/058791 A2 | * | 7/2004 |

OTHER PUBLICATIONS

Gold et al., "Animal Models for Autoimmune Demyelinating Disorders of the Nervous System," Molecular Medicine Today, 6, 88-91 (Feb. 2000).*
Link et al., "Rat Models as Tool to Develop New Immunotherapies," Immunological Reviews, 184, 117-128 (2001).*
Mix et al., "Gene-Expression Profiling of Experimental Autoimmune Encephalitis," Neurochemical Research, 27(10), 1157-1163 (Oct. 2002).*
Siddiqi, S.M. et al., "Search for New Purine- and Ribose-Modified Adenosine Analogues as Selective Agonists and Antagonists at Adenosine Receptors", J. Med. Chem, (1995), vol. 38, pp. 1174-1188.

* cited by examiner

*Primary Examiner*—L. E. Crane
(74) *Attorney, Agent, or Firm*—Browdy and Neimark

(57) ABSTRACT

Individuals suffering from multiple sclerosis may be treated by administration of an A3 adenosine receptor agonist (A3RAg), such as APNEA, AB-MECA, IB-MECA or Cl-IB-MECA. The A3RAg is preferably administered orally with a pharmaceutically acceptable carrier.

4 Claims, 1 Drawing Sheet

METHOD FOR TREATMENT OF MULTIPLE SCLEROSIS

This is a 371 of PCT/IL04/01160, filed on Dec. 23, 2004 which claims the benefit of U.S. provisional application Ser. No. 60/532,712, filed Dec. 29, 2003.

FIELD OF THE INVENTION

This invention relates to compounds and methods useful in the treatment of multiple sclerosis.

BACKGROUND OF THE INVENTION

Multiple sclerosis (MS) is a chronic, progressive, degenerative disease of the central nervous system (CNS), and particularly of the "white matter" tissue. It is considered an autoimmune disease characterized by inflammation and demyelination of the CNS leading to chronic neuralgic disturbances. Autoantibodies are generated by the immune system against antigens of myelin proteins such as myelin basic protein (MBP) which envelops the spinal cord.

Experimental autoimmune encephalomyelitis (EAE) is the commonly used animal model for MS. It may be induced in wild-type animals such as rodents by inoculation, or appear spontaneously in genetically susceptible strains.

Adenosine receptors are classified into four major classes: A1, A2a, A2b and A3. A3 adenosine receptors belong to the family of the $G_i$-protein associated cell surface receptors. Receptor activation leads to its internalization and the subsequent inhibition of adenylyl cyclase activity, cAMP formation and protein kinase A (PKA) expression, resulting in the initiation of various signaling pathways[1,2]. PKA contains a catalytic subunit PKAc which dissociates from the parent molecule upon activation with cAMP.

U.S. Pat. No. 5,506,214 (Beutler) discloses treatment of patients having MS with therapeutic agents containing substituted adenine derivatives such as 2-chloro-2'-deoxyadenosine (CdA). Treatment with CdA was shown to markedly ameliorate the disease condition. CdA was found to be a putative partial agonist at A1 receptors, as described in Siddiqi, S. M. et al, (1995) J. Med. Chem. 38:1174-1188. The $K_i$ values of CdA for the various adenosine receptors were 7.4 µM at the A1 receptor, 20 µM at the A2a receptor and 207 µM at the A3 receptor.

U.S. Patent Application No. 20020094974 (Castelhano, et al) discloses new N-6 substituted 7-deazapurine derivatives which are A3 adenosine receptor antagonists. These compounds may be used for treating diseases associated with the A3 adenosine receptor, including neurological disorders such as MS.

GENERAL DESCRIPTION OF THE INVENTION

The present invention is based on the surprising finding that administration of A3 adenosine receptor agonist (A3RAg) alleviates symptoms of multiple sclerosis.

Thus, the present invention concerns, by one embodiment, a method for the treatment of multiple sclerosis (MS) in a human subject, comprising administering to an individual in need of such treatment an effective amount of an A3RAg.

The term: "multiple sclerosis" (MS) refers in the context of the present invention to the inflammatory disease of the CNS in which the nerve insulating myelin sheath is partially lost, resulting in various pathological symptoms. MS includes various types of the disease such as relapsing/remitting (RRMS), secondary progressive (SPMS), progressive relapsing (PRMS) and primary progressive (PPMS).

The terms "treatment" or "neuralgic protection" in the context of the present invention refer to any improvement in the clinical symptoms of the disease, and/or a reduction in the rate of deterioration or the relapse rate of the MS patient, as well as any improvement in the well being of the patients. For example, an improvement may be manifested by one or more of the following: decrease in muscle weakness, decrease in muscle spasms, reduction of spasticity, improvement of balance and improvement in memory.

The term "adenosine A3 receptor agonist" (A3RAg) in the context of the present invention refers to any molecule capable of specifically binding to the adenosine A3 receptor ("A3R"), thereby fully or partially activating said receptor. The A3RAg is thus a molecule that exerts its prime effect through the binding and activation of the A3R. This means that at the doses it is being administered it essentially binds to and activates only the A3R. In a preferred embodiment, an A3RAg has a binding affinity ($K_i$) to the human adenosine A3 receptor in the range of less than 100 nM, typically less than 50 nM, preferably less than 20 nM, more preferably less than 10 nM and ideally less than 5 nM. The lower the Ki, the lower the dose of the A3RAg (that may be used) that will be effective in activating the A3R and thus achieving a therapeutic effect. Thus at times, A3RAgs that have a $K_i$ to the human A3R of less than 2 nM and even less than 1 nM may be preferred.

It should be noted that some A3RAgs can also interact with and activate other receptors with lower affinities (namely a higher Ki). A molecule will be considered an A3RAg in the context of the invention (namely a molecule that exerts its prime effect through the binding and activation A3R) if its affinity to the A3R is at least 3 times (i.e. its Ki to the A3R is at least 3 times lower), preferably 10 times, desirably 20 times and most preferably at least 50 times larger than the affinity to any other of the adenosine receptors (i.e. A1, A2a and A2b).

The affinity of an A3RAg to the human A3R as well as its relative affinity to the other human adenosine receptors (A1, A2a and A2b) can be determined by a number of assays, such as a binding assay. Examples of binding assays include providing membranes or cells having the receptor and measuring the ability of the A3RAg to displace a bound radioactive agonist; utilizing cells that display the respective human adenosine receptor and measuring, in a functional assay, the ability of the A3RAg to activate or deactivate, as the case may be, downstream signaling events such as the effect on adenylate cyclase measured through increase or decrease of the cAMP level; etc. Clearly, if the administered level of an A3RAg is increased such that its blood level reaches a level approaching that of the Ki of the A1, A2a and A2b adenosine receptors, activation of these receptors may occur following such administration, in addition to activation of the A3R An A3RAg is thus preferably administered at a dose such that the blood level that will be attained will give rise to essentially only A3R activation.

The characteristic of some adenosine A3 receptor agonists and methods of their preparation are described in detail in, inter alia, U.S. Pat. No. 5,688,774; U.S. Pat. No. 5,773,423, U.S. Pat. No. 5,573,772, U.S. Pat. No. 5,443,836, U.S. Pat. No. 6,048,865, WO 95/02604, WO 99/20284 and WO 99/06053, WO 97/27173, all of which are incorporated herein by reference.

According to one embodiment of the invention, the A3RAg is a compound that exerts its prime effect through the binding and activation A3R and is a purine derivative falling within the scope of the general formula (I):

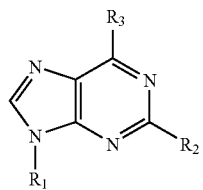

(I)

wherein, $R_1$ represents an alkyl, hydroxyalkyl, carboxyalkyl or cyanoalkyl or a group of the following general formula (II):

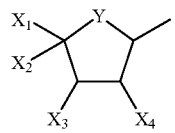

(II)

in which:

Y represents oxygen, sulfur or $CH_2$;

$X_1$ represents H, alkyl, $R^a R^b NC(=O)—$ or $HOR^c—$, wherein $R^a$ and $R^b$ may be the same or different and are selected from the group consisting of hydrogen, alkyl, amino, haloalkyl, aminoalkyl, BOC-aminoalkyl, and cycloalkyl or are joined together to form a heterocyclic ring containing two to five carbon atoms; and $R^c$ is selected from the group consisting of alkyl, amino, haloalkyl, aminoalkyl, BOC-aminoalkyl, and cycloalkyl;

$X_2$ is H, hydroxyl, alkylamino, alkylamido or hydroxyalkyl;

$X_3$ and $X_4$ represent independently hydrogen, hydroxyl, amino, amido, azido, halo, alkyl, alkoxy, carboxy, nitrilo, nitro, trifluoro, aryl, alkaryl, thio, thioester, thioether, —OCOPh, —OC(=S)OPh or both $X_3$ and $X_4$ are oxygens connected to >C=S to form a 5-membered ring, or $X_2$ and $X_3$ form the ring of formula (III):

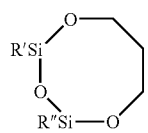

(III)

where R' and R" represent independently an alkyl group;

$R_2$ is selected from the group consisting of hydrogen, halo, alkylether, amino, hydrazido, alkylamino, alkoxy, thioalkoxy, pyridylthio, alkenyl; alkynyl, thio, and alkylthio; and $R_3$ is a group of the formula —$NR_4R_5$ wherein $R_4$ is a hydrogen atom or a group selected from alkyl, substituted alkyl or aryl-NH—C(Z)—, with Z being O, S, or $NR^a$ with $R^a$ having the above meanings; wherein when $R_4$ is hydrogen, then $R_5$ is selected from the group consisting of R- and S-1-phenylethyl, benzyl, phenylethyl or anilide groups unsubstituted or substituted in one or more positions with a substituent selected from the group consisting of alkyl, amino, halo, haloalkyl, nitro, hydroxyl, acetoamido, alkoxy, and sulfonic acid or a salt thereof; benzodioxanemethyl, furfuryl, L-propylalanyl-aminobenzyl, β-alanylamino-benzyl, T-BOC-β-alanylaminobenzyl, phenylamino, carbamoyl, phenoxy or cycloalkyl; or $R_5$ is a group of the following formula:

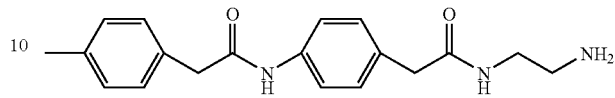

or when $R_4$ is an alkyl or aryl-NN—C(Z)—, then, $R_5$ is selected from the group consisting of heteroaryl-$NR^a$—C(Z)—, heteroaryl-C(Z)—, alkaryl-$NR^a$—C(Z)—, alkaryl-C(Z)—, aryl-NR—C(Z)— and aryl-C(Z)—; Z representing an oxygen, sulfor or imine; or a physiologically acceptable salt of the above compound.

According to one preferred embodiment, the A3RAg is a nucleoside derivative of the general formula (IV):

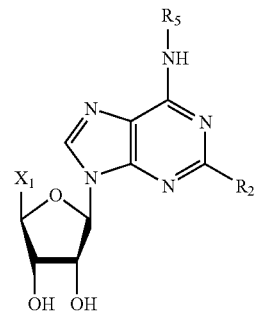

wherein $X_1$, $R_2$ and $R_5$ are as defined above, and physiologically acceptable salts of said compound.

The non-cyclic carbohydrate groups (e.g. alkyl, alkenyl, alkynyl, alkoxy, aralkyl, alkaryl, alkylamine, etc) forming part of the substituent of the compounds of the present invention are either branched or unbranched, preferably containing from one or two to twelve carbon atoms.

When referring to "physiologically acceptable salts" of the compounds employed by the present invention it is meant any non-toxic alkali metal, alkaline earth metal, and ammonium salt commonly used in the pharmaceutical industry, including the sodium, potassium, lithium, calcium, magnesium, barium ammonium and protamine zinc salts, which are prepared by methods known in the art. The term also includes non-toxic acid addition salts, which are generally prepared by reacting the compounds of this invention with a suitable organic or inorganic acid. The acid addition salts are those which retain the biological effectiveness and qualitative properties of the free bases and which are not toxic or otherwise undesirable. Examples include, inter alia, acids derived from mineral acids, hydrochloric, hydrobromic, sulfuric, nitric, phosphoric, metaphosphoric and the like. Organic acids include, inter alia, tartaric, acetic, propionic, citric, malic, malonic, lactic, fumaric, benzoic, cinnamic, mandelic, glycolic, gluconic, pyruvic, succinic salicylic and arylsulphonic, e.g. p-toluenesulphonic, acids.

Specific examples of A3RAg which may be employed according to general formula (IV) of the present invention include, without being limited thereto, $N^6$-2-(4-aminophenyl)ethyladenosine (APNEA), $N^6$-(4-amino-3-iodobenzyl)

adenosine-5'-(N-methyluronanide) (AB-MECA), $N^6$-(3-iodobenzyl)-adenosine-5'-N-methyluronamide (IB-MECA) and 2-chloro-$N^6$-(3-iodobenzyl)-adenosine-5'-N-methyluronamide (Cl-IB-MECA).

According to another embodiment, the A3RAg may be an oxide derivative of adenosine, such as $N^6$-benzyladenosine-5'-N-alkyluronamide-$N^1$-oxide or $N^6$-benzyladenosine-5'-N-dialkyluro wherein the 2-purine position may be substituted with an alkoxy, amino, alkenyl, alkynyl or halogen.

The administration of said A3RAg to a patient may be together with a pharmaceutically acceptable carrier. In the case where the administration is oral, the carrier is one that is acceptable for oral administration.

By the term "pharmaceutically acceptable carrier" it is meant any one of inert, non-toxic materials, which do not react with the A3RAg and which can be added to formulations as diluents or carriers or to give form or consistency to the formulation. An oral formulation may be in the form of a pill, capsule, in the form of a syrup, an aromatic powder, and other various forms. The carrier is selected at times based on the desired form of the formulation. The carrier may also at times have the effect of the improving the delivery or penetration of the active ingredient to the target tissue, for improving the stability of the drug, for slowing clearance rates, for imparting slow release properties, for reducing undesired side effects etc. The carrier may also be a substance that stabilizes the formulation (e.g. a preservative), for providing the formulation with an edible flavor, etc. The carriers may be any of those conventionally used and is limited only by chemical-physical considerations, such as solubility and lack of reactivity with the A3RAg, and by the route of administration. The carrier may include additives, colorants, diluents, buffering agents, disintegrating agents, moistening agents, preservatives, flavoring agents, and pharmacologically compatible carriers. In addition, the carrier may be an adjuvant, which, by definition are substances affecting the action of the active ingredient in a predictable way. Typical examples of carriers include (a) liquid solutions, where an effective amount of the active substance is dissolved in diluents, such as water, saline, natural juices, alcohols, syrups, etc.; (b) capsules (e.g. the ordinary hard- or soft-shelled gelatin type containing, for example, surfactants, lubricants, and inert fillers), tablets, lozenges (wherein the active substance is in a flavor, such as sucrose and acacia or tragacanth or the active substance is in an inert base, such as gelatin and glycerin), and troches, each containing a predetermined amount of the A3RAg as solids or granules; (c) powders; (d) suspensions in an appropriate liquid; (e) suitable emulsions; (f) liposome formulation; and others.

The term "effective amount" in the context of the present invention refers to an amount of A3RAg which results in neuralgic protection of the patient from the pathological symptoms of MS. The "effective amount" can be readily determined, in accordance with the invention, by administering to a plurality of tested subjects various amounts of the A3RAg and then plotting the physiological response (for example an integrated "MS index" combining several of the therapeutically beneficial effects) as a function of the amount. Alternatively, the effective amount may also be determined, at times, through experiments performed in appropriate animal models and then extrapolating to human beings using one of a plurality of conversion methods; or by measuring the plasma concentration or the area under the curve (AUC) of the plasma concentration over time and calculating the effective dose so as to yield a comparable plasma concentration or AUC. As known, the effective amount may depend on a variety of factors such as mode of administration (for example, oral administration may require a higher dose to achieve a given plasma level or AUC than an intravenous administration); the age, weight, body surface area, gender, health condition and genetic factors of the subject; other administered drugs; etc.

In the following, unless otherwise indicated, dosages are indicated in weight/Kg, meaning weight of administered A3RAg (e.g. IB-MECA or Cl-IB-MECA) per kilogram of body weight of the treated subject in each administration. For example, mg/Kg and microgram/Kg denote, respectively, milligrams of administered agent and micrograms of administered agent per kilogram of body weight of the treated subject.

In mice the effective amount is typically less than about 1000 and preferably less than about 500 microgram/Kg. A typical dose would be in the range of about 1 microgram/Kg to about 200 microgram/Kg, with a preferred dose being in the range of about 5 microgram/Kg to about 150 microgram/Kg. The corresponding effective amount in a human will be a human equivalent amount to that observed in mice, which may be determined in a manner as explained bellow.

The term "human equivalent" refers to the dose that produces in human the same effect as featured when a dose of 0.001-1 mg/Kg of an A3RAg is administered to a mouse or a rat. As known, this dose depends and may be determined on the basis of a number of parameters such as body mass, body surface area, absorption rate of the active agent, clearance rate of the agent, rate of metabolism and others.

The human equivalent may be calculated based on a number of conversion criteria as explained bellow; or may be a dose such that either the plasma level will be similar to that in a mouse following administration at a dose as specified above; or a dose that yields a total exposure (namely area under the curve—AUC—of the plasma level of said agent as a function of time) that is similar to that in mice at the specified dose range.

It is well known that an amount of X mg/Kg administered to rats can be converted to an equivalent amount in another species (notably humans) by the use of one of possible conversions equations well known in the art. Examples of conversion equations are as follows:

Conversion I:

| Species | Body Wt. (Kg) | Body Surf. Area ($m^2$) | Km Factor |
|---|---|---|---|
| Mouse | 0.2 | 0.0066 | 3.0 |
| Rat | 0.15 | 0.025 | 5.9 |
| Human Child | 20.0 | 0.80 | 25 |
| Adult | 70.0 | 1.60 | 37 |

Body Surface area dependent Dose conversion: Rat (150 g) to Man (70 Kg) is 1/7 the rat dose. This means that, for example, 0.001-1 mg/Kg in rats equals to about 0.14-140 microgram/Kg in humans. Assuming an average human weight of 70 Kg, this would translate into an absolute dosage for humans of about 0.01 to about 10 mg.

Conversion II:

The following conversion factors: Mouse=3, Rat=67. Multiply the conversion factor by the animal weight to go from mg/Kg to mg/$m^2$ for human dose equivalent.

| Species | Weight (Kg) | BSA (m²) |
|---|---|---|
| Human | 70.00 | 1.710 |
| Mouse | 0.02 | 0.007 |
| Rat | 0.15 | 0.025 |
| Dog | 8.00 | 0.448 |

According to this equation the amounts equivalent to 0.001-1 mg/Kg in rats for humans are 0.16-64 µg/Kg; namely an absolute dose for a human weighing about 70 Kg of about 0.011 to about 11 mg, similar to the range indicated in Conversion I.

Conversion III:

Another alternative for conversion is by setting the dose to yield the same plasma level or AUC as that achieved following administration to an animal. For example, based on measurement made in mice following oral administration of IB-MECA and based on such measurements made in humans in a clinical study in which IB-MECA was given to healthy male volunteers it can be concluded that a dose of 1 microgram/Kg-1,000 microgram/KG in mice is equivalent to a human dose of about 0.14-140 microgram/Kg, namely a total dose for a 70 Kg individual of 0.01-10 mg.

It should be noted that in addition to said therapeutic method, also encompassed within the present invention is a pharmaceutical composition for the treatment of multiple sclerosis that comprises an effective amount of an A3RAg as defined above and a pharmaceutically acceptable carrier; as well as the use of said A3RAg for the preparation of a pharmaceutical composition for administration to a subject suffering from multiple sclerosis and being in need of a neuralgic protective treatment. As will be appreciated, the effective amount in the pharmaceutical composition will depend on the intended therapeutic regimen and the desired therapeutic dose. By way of example, where the dose is 1 mg per day and the. desired administration regimen is once daily, the amount of active agent in the pharmaceutical composition will be 1 mg. In cases where it is intended to administer this daily dose in 2 daily administrations, the amount of the active agent in the pharmaceutical composition will be 0.5 mg.

The invention will now be exemplified in the following description of experiments that were carried out in accordance with the invention. It is to be understood that these examples are intended to be in the nature of illustration rather than of limitation. Obviously, many modifications and variations of these examples are possible in light of the above teaching. It is therefore, to be understood that within the scope of the appended claims, the invention may be practiced otherwise, in a myriad of possible ways, than as specifically described hereinbelow.

BRIEF DESCRIPTION OF THE DRAWING

In order to understand the invention and to see how it may be carried out in practice, a preferred embodiment will now be described, by way of non-limiting example only, with reference to the accompanying drawing, in which.

DETAILED DESCRIPTION OF THE INVENTION

EXAMPLE I

Materials and Methods

Figure 1:
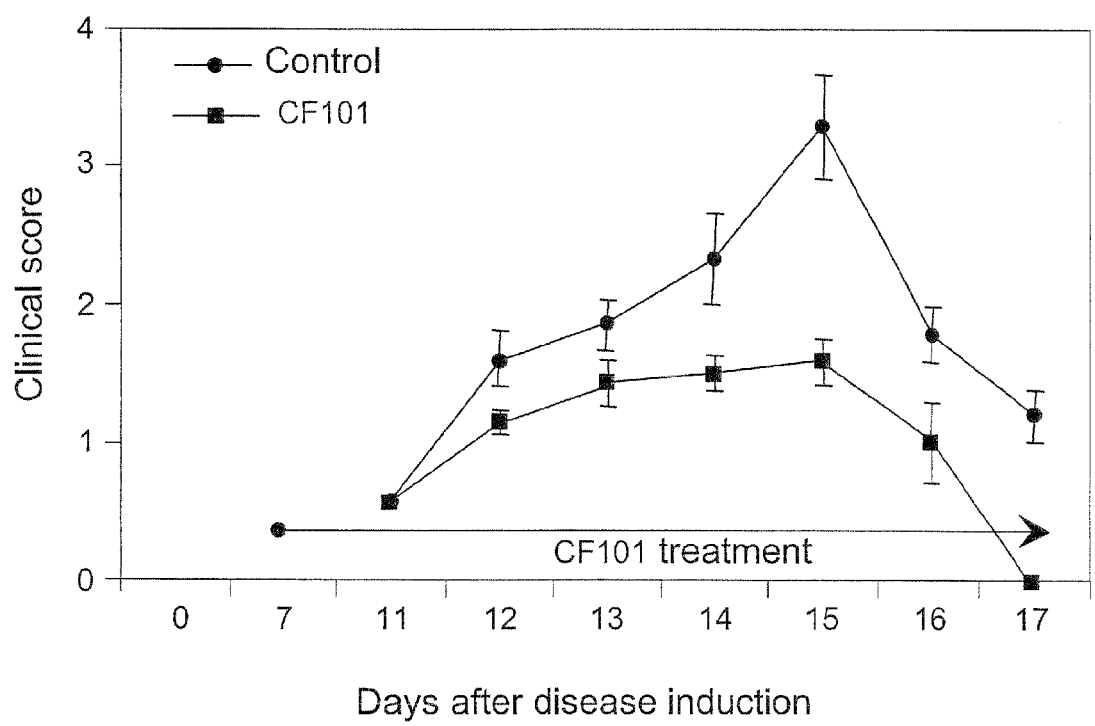
FIG. 1 is a graph illustrating the clinical symptoms of rats suffering from EAE as a function of time, which were treated (□) or not treated (♦) with the A3RAg IB-MECA (CF101).

IB-MECA, produced as a clinical grade material under clinical good manufacturing practice (cGMP) conditions by Albany Molecular Research, Albany, New York, USA on behalf of Can-Fite BioPharma, Ltd., Israel (this material is designated as CF101). A stock solution of 10 µM was prepared in DMSO and further dilutions were made in RPMI medium.

Induction of Experimental Autoimmune Encephalomylitis (EAE)

EAE was induced by intradermal injection at the base of the tail of female Lewis rats (8 weeks old) with an emulsion consisting of the following for each rat: 100 µg myelin basic protein (MBP) from guinea pig (M2295; Sigma), 0.1 ml Complete Freund's adjuvant (CFA; F5506, Sigma), and 0.2 mg of *Mycobacterium tuberculosis* H37 Ra (*M. tuberculosis*, 3114, Difco). The emulsion was injected in two halves into the medial footpad of each hind limb of the rats. CF101 treatment PBS solution (10 µg/kg, PO, BID (twice daily)) started at day 7 after disease induction. Control received PBS.

The rats developed clinical EAE symptoms which were graded into the following categories: 0, no neurological symptoms; 1, loss of tail tonus and paralysis of the whole tail; 2, hind limbs weakness; 3, hind limbs paralysis; 4, quadriplegia; 5, moribund.

Results

The immunized rats developed acute monophasic EAE within 10 days after immunization that lasted for 5 days. A remarkably low clinical score in the CF101 treated group in comparison to the control group was noted. The difference in the maximal clinical score between the CF101 and the control groups was significant with P<0.01 using the Student's t test, and the severity of the disease in the treated group was significantly reduced.

The invention claimed is:

1. A method for treating an individual suffering from multiple sclerosis (MS) comprising administering to said individual an $A_3$ adenosine receptor agonist ($A_3$RAg) wherein said $A_3$RAg is a compound within the scope of the general formula (I):

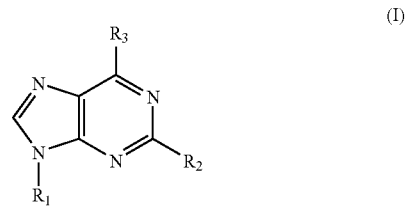

(I)

wherein, $R_1$ represents an alkyl, hydroxyalkyl, carboxyalkyl or cyanoalkyl or a group of the following general formula (II):

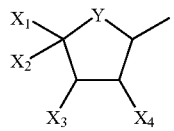

in which:

Y represents an oxygen, sulfur or $CH_2$;

$X_1$ represents H, alkyl, $R^aR^bNC(=O)$— or $HOR^c$—, wherein
  $R^a$ and $R^b$ may be the same or different and are hydrogen, alkyl, amino, haloalkyl, aminoalkyl, BOC-aminoalkyl, or cycloalkyl or are joined together to form a heterocyclic ring containing two to five carbon atoms; and
  $R^c$ is alkyl, amino, haloalkyl, aminoalkyl, BOC-aminoalkyl, or cycloalkyl;

$X_2$ is H, hydroxyl, alkylamino, alkylamido or hydroxyalkyl;

$X_3$ and $X_4$ represent independently hydrogen, hydroxyl, amino, amido, azido, halo, alkyl, alkoxy, carboxy, nitrilo, nitro, trifluoro, aryl, alkaryl, thio, thioester, thioether, —OCOPh, or —OC(=S)OPh or both $X_3$ and $X_4$ are oxygens connected to >C=S to form a 5-membered ring, or $X_2$ and $X_3$ form the ring of formula (III):

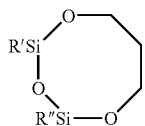

where R' and R" represent independently an alkyl group;

$R_2$ is hydrogen, halo, alkylether, amino, hydrazido, alkylamino, alkoxy, thioalkoxy, pyridylthio, alkenyl, alkynyl, thio, or alkylthio; and $R_3$ is a group of the formula —$NR_4R_5$, wherein $R_4$ is a hydrogen atom or alkyl, substituted alkyl or aryl-NH—C(Z)—, with Z being O, S, or $NR^a$ with $R^a$ having the above meanings;

with the proviso that when $R_4$ is hydrogen then $R_5$ is an R— or S-1-phenylethyl, benzyl, phenylethyl or anilide group, unsubstituted or substituted in one or more positions with a substituent that is alkyl, amino, halo, haloalkyl, nitro, hydroxyl, acetoamido, alkoxy, or sulfonic acid or a salt thereof; benzodioxanemethyl, furfuryl, L-propylalanylaminobenzyl, β-alanylaminobenzyl, T-BOC-β-alanylaminobenzyl, phenylamino, carbamoyl, phenoxy or cycloalkyl; or $R_5$ is a group of the following formula:

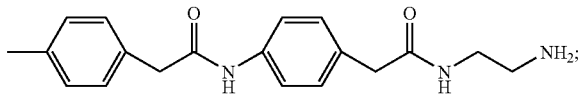

and with the further proviso that when $R_4$ is an alkyl or aryl-NH—C(Z)—, then, $R_5$ is heteroaryl-$NR^a$—C(Z)—, heteroaryl-C(Z)—, alkaryl-$NR^a$—C(Z)—, alkaryl-C(Z)—, aryl-NR—C(Z)—, or aryl-C(Z)—, Z representing an oxygen, sulfur or imine;

or a physiologically acceptable salt of the above compound.

2. The method of claim 1, wherein said A3RAg is orally administered.

3. The method of claim 1, wherein said A3RAg is a nucleoside derivative of the general formula (IV):

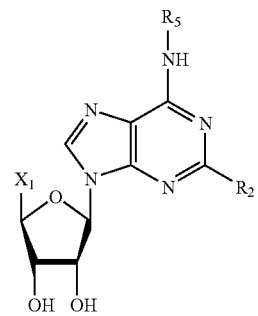

wherein, $X_1$ represents H, alkyl, $R^aR^bNC(=O)$— or $HOR^c$—, wherein
  $R^a$ and $R^b$ may be the same or different and are hydrogen, alkyl, amino, haloalkyl, aminoalkyl, BOC-aminoalkyl, or cycloalkyl or are joined together to form a heterocyclic ring containing two to five carbon atoms; and
  $R^c$ is alkyl, amino, haloalkyl, aminoalkyl, BOC-aminoalkyl, or cycloalkyl;

$R^2$ is hydrogen, halo, alkylether, amino, hydrazido, alkylamino, alkoxy, thioalkoxy, pyridylthio, alkenyl, alkynyl, thio, or alkylthio; and $R_5$ is an R- or S-1-phenylethyl, benzyl, phenylethyl or anilide group, unsubstituted or substituted in one or more positions with a substituent that is alkyl, amino, halo, haloalkyl, nitro, hydroxyl, acetoamido, or sulfonic acid or a salt thereof; benzodioxanemethyl, furfuryl, L-propylalanylaminobenzyl, β-alanylaminobenzyl, T-BOC-β-alanylaminobenzyl, phenylamino, carbamoyl, phenoxy or cycloalkyl; or $R_5$ is a group of the following formula:

and physiologically acceptable salts of said nucleoside derivative.

4. The method of claim 1, wherein said $A_3RAg$ is $N^6$-2-(4-aminophenyl)ethyladenosine (APNEA), $N^6$-(4-amino-3-iodobenzyl)adenosine-5'-(N-methyluronamide) (AB-MECA), $N^6$-(3-iodobenzyl)-adenosine-5'-N-methyluronamide (IB-MECA), or 2-chloro-$N^6$-(3-iodobenzyl)-adenosine-5'-N-methyluronamide (Cl-IB-MECA).

* * * * *